(12) United States Patent
Park

(10) Patent No.: US 6,183,749 B1
(45) Date of Patent: Feb. 6, 2001

(54) DIETARY SUPPLEMENT CONTAINING HERBAL EXTRACTS WHICH PROMOTES HEALTHY HAIR GROWTH ON THE SCALP

(76) Inventor: Cliff Jae Bum Park, 1037 S. Elden Ave., Los Angeles, CA (US) 90006

( * ) Notice: Under 35 U.S.C. 154(b), the term of this patent shall be extended for 0 days.

(21) Appl. No.: 09/507,489

(22) Filed: Feb. 17, 2000

(51) Int. Cl.⁷ ..................................................... A01N 65/00
(52) U.S. Cl. ........................................................... 424/195.1
(58) Field of Search .............................. 514/643; 424/61, 424/195.1, 404, 409, 472

(56) References Cited

U.S. PATENT DOCUMENTS

| | | | |
|---|---|---|---|
| 4,569,839 | * | 2/1986 | Grollier et al. ........................ 424/74 |
| 4,767,618 | * | 8/1988 | Grollier et al. ........................ 424/74 |
| 4,933,177 | * | 6/1990 | Grollier et al. ........................ 424/74 |

* cited by examiner

Primary Examiner—Jean C. Witz
Assistant Examiner—Patricia Patten
(74) Attorney, Agent, or Firm—Kim & Lee; Jerry H. Noh

(57) ABSTRACT

A composition of a dietary supplement comprising MAMMALIA PLACENTA prepared from the placenta of a mammal, FRUCTUS LIGUSTRI LUCIDI, SALVIAE MILTIORRHIZAE, PAEONIAE RUBRA, CINNAMOMI CASSIAE, MOUTAN RADICIS, and ALISMATIS PLANTAGO-AQUATICA. For increased benefit, the dietary supplement further comprising POLYGONI MULTIFLORI, FRUCTUS LYCII CHINENSIS, FRUCTUS MORI ALBAE, VACCARIAE SEGETALIS, PLATICODI GRANDIFLORI, COICIS LACHRYMA-JOBI, and ARTEMESIAE CAPILLARIS. The dietary supplement is for oral ingestion and can be prepared in the form of a tablet, capsule, powder or syrup.

9 Claims, No Drawings

DIETARY SUPPLEMENT CONTAINING HERBAL EXTRACTS WHICH PROMOTES HEALTHY HAIR GROWTH ON THE SCALP

BACKGROUND OF THE INVENTION

I. Field of the Invention

This invention pertains generally to dietary food supplements. More specifically, the invention concerns an herbal dietary food product which promotes healthy hair growth on one's scalp.

II. Description of the Prior Art

The use of herbal extracts for health benefits have been known for thousands of years in East Asian countries such as China, Korea, and Japan. The utilization of herbal extracts as dietary supplements for promoting various sorts of health benefits have been gaining wide acceptance in western countries.

Several patents have been issued in the United States which utilize herbal extracts for health benefits. One such patent is U.S. Pat. No. 5,869,059 issued to Garza which teaches an herbal composition beneficial for the treatment of hemorrhoid. Another patent is U.S. Pat. No. 5,770,207 issued to Bewicke which teaches a dietary supplement containing herbal extracts that serves as a general relaxant. None of the prior art teaches an herbal dietary supplement which promotes healthy hair growth on an individual's scalp.

Thus, it is a primary objective of the present invention to provide an orally ingestable composition which promotes healthy hair growth on the scalp of an individual's head.

BACKGROUND AND SUMMARY OF THE INVENTION

This invention provides a dietary supplement consisting of herbal extracts which promotes healthy hair growth on an individual's scalp. The dietary supplement comprises extracts from herbal plants which can be grouped into three categories according to their common functions.

The first category consists of herbal plants having properties which include providing nourishment to the hair. By their pharmaceutical names, they include POLYGONI MULTIFLORI, LIGUSTRI LUCIDI, LYCII CHINENSIS, and MORI ALBAE. POLYGONI MULTIFLORIA is prepared from a plant known by its botanical name as *Polygonum multiflorum* Thunb, and its known effect is in nourishing the liver and kidneys. LIGUSTRI LUCIDI is prepared from a plant known by its botanical name as *Ligustrum lucidum* Ait, and its known effect is in tonifying the liver and kidneys and in nourishing the blood. LYCII CHINENSIS is prepared from a plant known by its botanical name as Lycium chinese Mill, and its known effect is in nourishing the liver and kidneys. MORI ALBAE is prepared from a plant known by its botanical name as *Mori Alba* L, and its known effect is in nourishing the blood. Although not an herbal plant, MAMMALIA PLACENTA prepared from the placenta of mammals are known to have properties which provide nourishment to the hair. A popular mammalian placenta utilized is HOMINIS PLACENTA prepared from human placenta.

The second category consists of herbal plants having properties which include promoting improved blood circulation in the body. By their pharmaceutical names, they include SALVIAE MILTIORRHIZAE, PAEONIAE RUBRA, and VACCARIAE SEGETALIS. SALVIAE MILTIORRHIZAE is prepared from a plant known by its botanical name as *Salvia miltiorrhiza* Bge, and it is known to invigorate the blood and break up congealed blood. PAEONIAE RUBRA can be prepared from one of several plants known their botanical names as *Paeonia obovata* Maxim, *Paeonia lactiflora* Pall, *Paeonia Japonica* Miyabe et Takeda and *Paeonia veitchiii* Lynch, and it is known to invigorate the blood and dispel congealed blood. VACCARIAE SEGETALIS is prepared from a plant known by its botanical name as *Vaccariae segetalis* Garcke, and it is known to move blood and promote circulation of blood through its channels. VACCARIAE SEGETALIS is highly related to and utilized interchangeably with SEMEN MELANDRII, which is prepared from a plant known by its botanical name as *Melandryum firmum* ROHRB. SEMEN MELANDRII is known to move blood and promote circulation of blood through its channels.

The third category consists of herbal plants having properties which in terms of Eastern studies generally directs the direction of blood flow upward in the body. By their pharmaceutical names, they include PLATICODI GRANDIFLORI, COICIS LACHRYMA-JOBI, CINNAMOMI CASSIAE, MOUTAN RADICIS, ALISMATIS PLANTAGO-AQUATICAE, and ARTEMESIAE CAPILLARIS. PLATICODI GRANDIFLORI is prepared from a plant known by its botanical name as *Platycodon grandiflorum* A.DC., and one of its known characteristics is to direct the effect of other herbs upwards, causing them to affect the upper region of the body. COICIS LACHRYMA-JOBI can be prepared from one of several plants known by their botanical names as *Coix lachryma-jobi* L. and *Coix lachryma-Jobi*(L.) Var. mayuen (ROMAISTARF), and one of its known effect is to promote urination and strengthen the spleen. CINNAMOMI CASSIAE is prepared from a plant known by its botanical name as *Cinnamomum cassia* Presl., and one of its known effect is to generally warm the kidneys, spleen, and stomach, causing energy and blood flow to moves upward. MOUTAN RADICIS is prepared from a plant known by its botanical name *Paeonia suffruticosa* Andr., and one of its known effect is to generally cool the blood. ALISMATIS PLANTAGO-AQUATICAE can be prepared from one of several plants known by their botanical names as *Alisma Plantago-aquatica* L Var. oriental Samuels and *Alisma canaliculatum* All.Br.et Bouche, and one of its known effect is to promote urination and increase energy flow in the kidneys. ARTEMESIAE CAPILLARIS can be prepared from one of several plants known by their botanical names as *Artemisia capillaris* Thunb., *Artemisia scoparia* Waldst. Et Kitaib, and *Artemisia iwayomagi* Kitamura, and one of its known effect is to generally clear build up of heat in areas of the body such as the liver and gall bladder.

Each of the above listed herbal plants in pharmaceutical terms has a SEMEN (seed), CORTEX (stem cortex), RHIZOMA (rhizome or root), RADIX (root), and RAMULUS (branch) portion, and some have a FRUCTUS (fruit) portion. The different portions of each herbal plant are known to have different levels of efficacy on the body. The extract of each of the above identified herbs is prepared and decocted by traditional procedures known in the art which includes boiling, filtering, and forming concentrates. Each of the herbal plants and the mammalia placenta is commercially available in extracted form e.g., from Sheng Chang, a Taiwanese company.

The dietary supplement of the present invention comprises MAMMALIA PLACENTA prepared from the placenta of a mammal, FRUCTUS LIGUSTRI LUCIDI, SALVIAE MILTIORRHIZAE, PAEONIAE RUBRA, CINNAMOMI CASSIAE, MOUTAN RADICIS, and ALISMA- TIS PLANTAGO-AQUATICA. For increased benefit, the dietary supplement can further comprise POLYGONI MULTIFLORI, FRUCTUS LYCII CHINENSIS, FRUCTUS MORI ALBAE, VACCARIAE SEGETALIS, PLATICODI GRANDIFLORI, COICIS LACHRYMA-JOBI, and ARTEMESIAE CAPILLARIS. The composition of the present invention is for oral ingestion and can be prepared in the form of a tablet, capsule, powder, or syrup.

DESCRIPTION OF THE PREFERRED EMBODIMENT

In the preferred embodiment, the composition of the present invention is a dietary supplement which comprises MAMMALIA PLACENTA prepared from the placenta of a mammal, FRUCTUS LIGUSTRI LUCIDI, SALVIAE MILTIORRHIZAE, PAEONIAE RUBRA, CINNAMOMI CASSIAE, MOUTAN RADICIS, and ALISMATIS PLANTAGO-AQUATICA. For increased benefit, the dietary supplement can further comprise POLYGONI MULTIFLORI, FRUCTUS LYCII CHINENSIS, FRUCTUS MORI ALBAE, VACCARIAE SEGETALIS, PLATICODI GRANDIFLORI, COICIS LACHRYMA-JOBI, and ARTEMESIAE CAPILLARIS. The extract of each of the above identified herbs is prepared and decocted by traditional procedures known in the art which includes boiling, filtering, and forming concentrates.

To form the composition of the present invention the extracted concentrate of each herb is mixed according to the following measurements: four to sixteen weight parts HOMINIS PLACENTA, five to fourteen weight parts FRUCTUS LIGUSTRI LUCIDI, four to ten weight parts SALVIAE MILTIORRHIZAE, four to ten weight parts PAEONIAE RUBRA, three to ten weight parts CINNAMOMI CASSIAE, two to eight weight parts MOUTAN RADICIS, and four to twelve weight parts of ALISMATIS PLANTAGO-AQUATICA. The preferred quantity of each concentrate is eleven parts HOMINIS PLACENTA, nine weight parts FRUCTUS LIGUSTRI LUCIDI, eight weight parts SALVIAE MILTIORRHIZAE, seven weight parts PAEONIAE RUBRA, five weight parts CINNAMOMI CASSIAE, five weight parts MOUTAN RADICIS, and seven weight parts of ALISMATIS PLANTAGO-AQUATICA.

When the extracted concentrates of the additional herbs are added for increased benefit, they are added according to the following measurements: five to twelve weight parts POLYGONI MULTIFLORI, five to twelve weight parts FRUCTUS LYCII CHINENSIS, four to ten weight parts FRUCTUS MORI ALBAE, four to ten weight parts VACCARIAE SEGETALIS, two to eight weight parts PLATICODI GRANDIFLORI, five to ten weight parts COICIS LACHRYMA-JOBI, and three to eight weight parts ARTEMESIAE CAPILLARIS. The preferred quantity of each concentrate is ten weight parts POLYGONI MULTIFLORI, nine weight parts FRUCTUS LYCII CHINENSIS, five weight parts FRUCTUS MORI ALBAE, seven parts VACCARIAE SEGETALIS, four weight parts PLATICODI GRANDIFLORI, seven weight parts COICIS LACHRYMA-JOBI, and six weight parts ARTEMESIAE CAPILLARIS.

To achieve the highest efficacy, in the preferred embodiment, FRUCTUS LIGUSTRI LUDIDI is prepared from the plant *Ligustrum lucidum* Ait; SALVIAE MILTIORHIZAE is prepared from the RADIX of the plant *Salvia miltiorrhiza* Bge; PAEONIAE RUBRA is prepared from the RADIX of at least one of the plant selected from the group consisting of *Paeonia obovata* Maxim, *Paeonia lactiflora* Pall, *Paeonia Japonica* Miyabe et Takeda and *Paeonia veitchii* Lynch; CINNAMOMI CASSIAE is prepared from the plant *Cinnamomum Cassia*; MOUTAN RADICIS is prepared from the CORTEX of the plant *Paeonia suffruticosa* Andr.; ALISMATIS PLANTAGO-AQUATICAE is prepared from the RHIZOMA of at least one of the plant selected from the group consisting of *Alisma Plantago-aquatica* L.Var. oriental Samuels and *Alisma canaliculatum* All.Br. et Bouche; POLYGONI MULTIFLORI is prepared from the RADIX of the plant *Polygonum multiflorum* Thunb; FRUCTUS LYCII CHINENSIS is prepared from the plant *Lycium chinense* Mill; FRUCTUS MORI ALBAE is prepared from the plant *Mori Alba* L; VACCARIAE SEGETALIS is prepared from the SEMEN of the plant *Vaccariae segetalis* Garcke; PLATICODI GRANDIFLORI is prepared from the RADIX of the plant *Platycodon grandiflorum* A.DC.; COICIS LACIRYMA-JOBI is prepared from the SEMEN of the plant *Coix lachryma-Jobi*; and ARTEMESIAE CAPILLARIS is prepared from the HERBA of at least one of the plant selected from the group consisting of *Artemisia Capillaris* Thunb, *Artemisia scoparia* Waldst. Et Kitaib and *Artemisia iwayomogi* Kitamura.

The composition of the present invention is for ingestion in the form of a tablet, capsule, powder, or syrup. Conventionally known methods known in the art are used to prepare the composition in the different forms. The form in which the composition is prepared does not significantly affect its efficacy. The ideal daily total dosage is twelve to fifteen grams of the composition taken in three intervals of four to five grams. The composition should be taken daily on a regular basis to obtain maximum benefits. An average of four to five weeks is minimally required to note improvement in hair quality and growth.

While a preferred embodiment of the invention has been described and illustrated for purposes of clarity and example, it should be understood that many changes, substitutions and modifications to the described embodiment will be apparent to those having skill in the art in light of the foregoing disclosure without departing from the scope and spirit of the present invention which is defined by the claim which will follow.

What is claimed is:

1. A dietary supplement comprising:
   MAMMALIA PLACENTA, extracted from the placenta of a mammal;
   FRUCTUS LIGUSTRI LUDIDI, prepared from an extract of the plant *Ligustrum lucidum;*
   SALVIAE MILTIORHIZAE, prepared from an extract of the plant *Salvia miltiorrhiza* Bge;
   PAEONIAE RUBRA, prepared from an extract of at least one plant selected from the group consisting of *Paeonia obovata* Maxim, *Paeonia lactiflora* Pall, *Paeonia Japonica* Miyabe et Takeda and *Paeonia veitchii* Lynch;
   CINNAMOMI CASSIAE, prepared from an extract the plant *Cinnamomum Cassia;*
   MOUTAN RADICIS, prepared from an extract of the plant *Paeonia suffruticosa* Andr., and
   ALISMATIS PLANTAGO-AQUATICAE, is prepared from an extract of at least one plant selected from the group consisting of *Alisma Plantago-aquatica* L.Var. oriental Samuels and *Alisma canaliculatum* All.Br. et Bouche.

2. A dietary supplement as described in claim 1 wherein said mammalian placenta is HOMINIS PLACENTA, extracted from human placenta.

3. A dietary supplement as described in claim 1 wherein said supplement is in the form of a tablet.

4. A dietary supplement as described in claim 1 wherein said supplement is in the form of a capsule.

5. A dietary supplement as described in claim 1 wherein said supplement is in the form of an aqueous syrup.

6. A dietary supplement as described in claim 1 wherein said supplement is in the form of a powder.

7. A dietary supplement as described in claim 1 additionally comprising:

POLYGONI MULTIFLORI, prepared from an extract of the plant *Polygonum multiflorum* Thunb;

FRUCTUS LYCII CHINENSIS, prepared from an extract of the plant *Lycium chinense* Mill, FRUCTUS MORI ALBAE, prepared from an extract of the plant *Mori Alba* L;

VACCARIAE SEGETALIS, prepared from an extract of the plant *Vaccariae segetalis* Garcke;

PLATICODI GRANDIFLORI, prepared from an extract of the plant *Platycodon grandiflorum* A.DC.;

COICIS LACHRYMA-JOBI, prepared from an extract of the plant *Coix lachryma-Jobi*; and ARTEMESIAE CAPILLARIS, prepared from an extract of at least one of the plant selected from the group consisting of *Artemisia Capillaris* Thunb, *Artemisia scoparia* Waldst. Et Kitaib and *Artemisia iwayomogi* Kitamura.

8. A dietary supplement as described in claim 1 wherein:

SALVIAE MILTIORHIZAE is prepared from the RADIX of the plant *Salvia miltiorrhiza* Bge, PAEONIAE RUBRA is prepared from the RADIX of at least one of the plant selected from the group consisting of *Paeonia obovata* Maxim, *Paeonia lactiflora* Pall, *Paeonia Japonica* Miyabe et Takeda and *Paeonia veitchii* Lynch;

MOUTAN RADICIS is prepared from the CORTEX of the plant *Paeonia suffruticosa* Andr.; and ALISMATIS PLANTAGO-AQUATICAE is prepared from the RHIZOMA of at least one of the plant selected from the group consisting of *Alisma Plantago-aquatica* L.Var. oriental Samuels and *Alisma canaliculatum* All.Br. et Bouche.

9. A dietary supplement as described in claim 7 wherein:

POLYGONI MULTIFLORI is prepared from the RADIX of the plant *Polygonum multiflorum* Thunb;

VACCARIAE SEGETALIS is prepared from the SEMEN of the plant *Vaccariae segetalis* Garcke;

PLATICODI GRANDIFLORI is prepared from the RADIX of the plant *Platycodon grandiflorum* A.DC.;

COICIS LACHRYMA-JOBI is prepared from the SEMEN of the plant *Coix lachryma-Jobi*; and ARTEMESIAE CAPIILLARIS is prepared from the HERBA of at least one of the plant selected from the group consisting of *Artemisia Capillaris* Thunb, *Artemisia scoparia* Waldst. Et Kitaib and *Artemisia iwayomogi* Kitamura.

* * * * *